US008203603B2

(12) United States Patent
Harbert et al.

(10) Patent No.: US 8,203,603 B2
(45) Date of Patent: Jun. 19, 2012

(54) AUGMENTED REALITY INDUSTRIAL OVERLINE SYSTEMS AND METHODS

(75) Inventors: Sim Harbert, Decatur, GA (US); Blair MacIntyre, Atlanta, GA (US); Douglas F. Britton, Roswell, GA (US); Daniel L. Shaw, Brooklyn, NY (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 12/321,566

(22) Filed: Jan. 22, 2009

(65) Prior Publication Data

US 2011/0050872 A1   Mar. 3, 2011

Related U.S. Application Data

(60) Provisional application No. 61/022,990, filed on Jan. 23, 2008.

(51) Int. Cl.
*H04N 7/18* (2006.01)
(52) U.S. Cl. ............... 348/91; 348/89; 348/92
(58) Field of Classification Search ............ 348/86, 348/91, 92, 89
See application file for complete search history.

(56) References Cited

U.S. PATENT DOCUMENTS

| 6,493,641 | B1 * | 12/2002 | Singh et al. ............. 702/32 |
| 7,071,462 | B2 * | 7/2006 | Young ............. 250/252.1 |
| 7,177,444 | B2 * | 2/2007 | Bonner et al. ............. 382/101 |
| 7,527,205 | B2 * | 5/2009 | Zhu et al. ............. 235/462.14 |
| 2008/0152082 | A1 * | 6/2008 | Bouchard et al. ............. 378/57 |
| 2010/0055259 | A1 * | 3/2010 | Bourg, Jr. ............. 426/231 |

* cited by examiner

*Primary Examiner* — Viet Vu
(74) *Attorney, Agent, or Firm* — Ryan A. Schneider, Esq.; Troutman Sanders LLP

(57) ABSTRACT

Disclosed are product processing systems and methods for monitoring, inspecting and controlling baking, cooking and routing processes, and the like. Products are placed on and moved by a conveyor. Images of the moving products are generated, such as by an image acquisition system. The images are processed by a symbol generation system. Symbols are then displayed on selected moving products based upon predetermined criteria. The systems and methods may be used to process oven-cooked or oven-baked products to identify (via the projected symbols) products that are defective or otherwise unacceptable. The product processing systems may be used to process packages or items having barcodes or other identifying labels to display routing or other identifying information on the moving products.

18 Claims, 12 Drawing Sheets

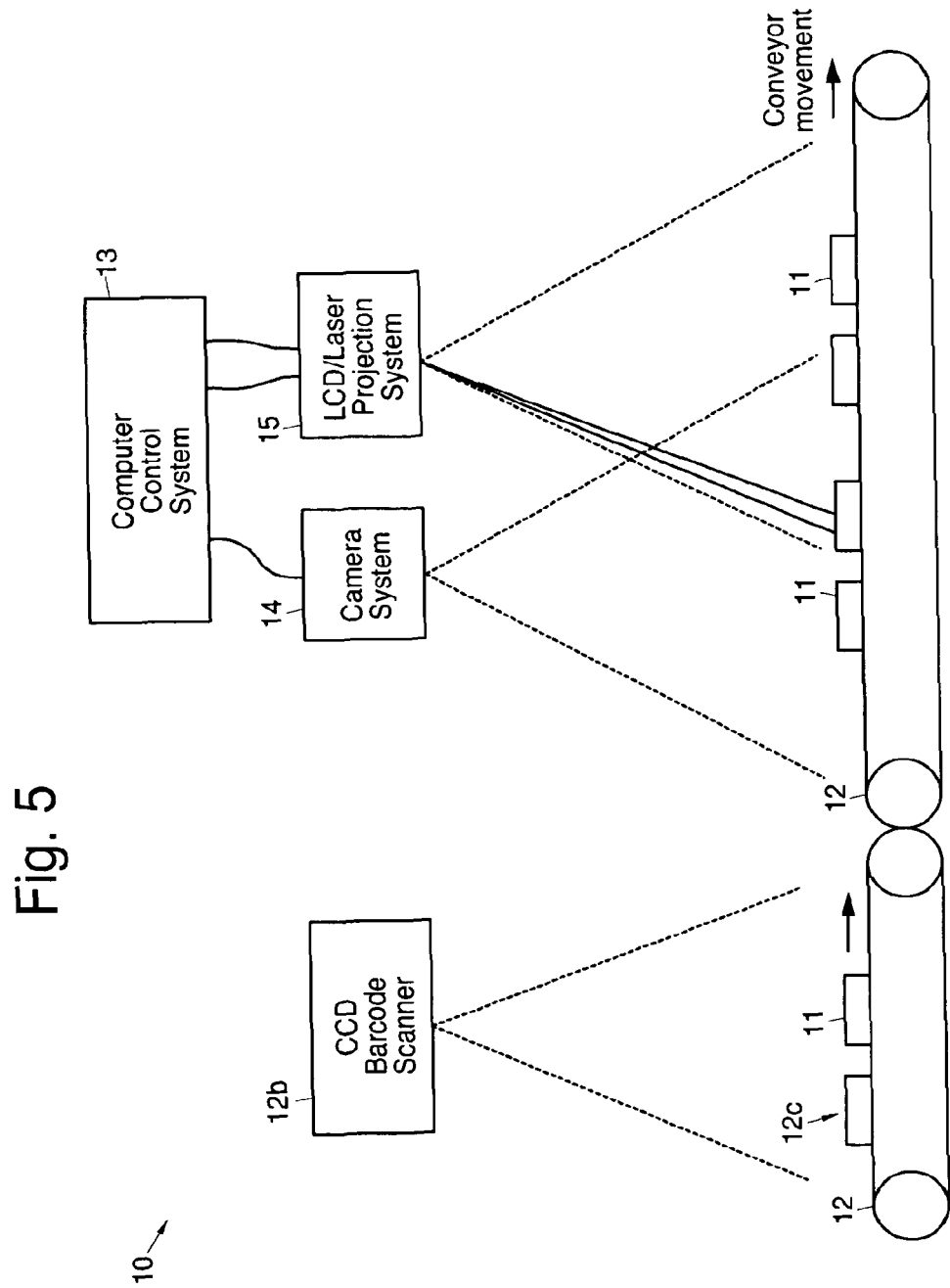

Laser rectangle (dashed box)

Example

Checkerboard square: 3 x 3 world units (cm, inches, etc)

Laser rectangle: 3 x 2 checkerboard squares (tell software)

Laser rectangle: 30 x 20 laser units (known by software)

3 x 2 checkerboard squares = 30 x 20 laser units 1 checkerboard square = 10 x 10 laser units 3 x 3 world units = 10 x 10 laser units 1 laser unit = .3 world units or 1 world unit = 3.33 laser units

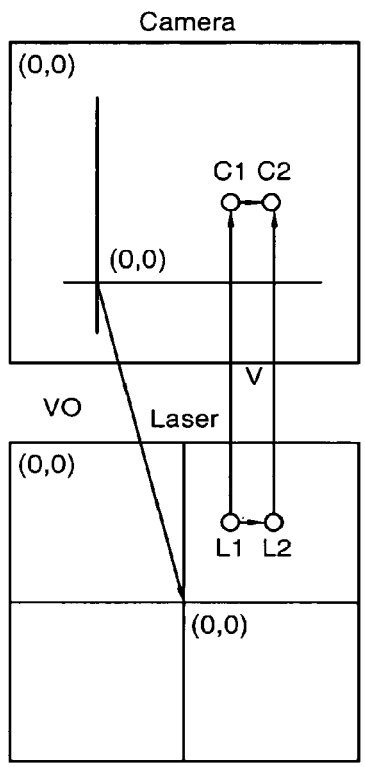

Camera

Example

Frame respective units

C1 = (100,100) in Camera
C2 = (105,100) in Camera
L1 = (10,20) in Laser
L2 = (20,20) in Laser

Fig. 6c

Camera software picks origin of world units and assigns C1 to WC1 and C2 to WC2

WC1 = (30,10)
WC2 = (35,10)

The length of the yardstick is known:

V = (0,300)

Calculate where WL1 and WL2 are using vector V:

WL1 = C2 - V
WL2 = C2 - V
WL1 = (30,10) - (0,300) = (30,-290)
WL2 = (35,10) - (0,300) = (35,-290)

Since the scaling is known, the Laser origin can be found in world units, and the vector VO which defines the offset VO1 = WL1 − (L1 * scaling)
VO2 = WL2 − (L2 * scaling)
VO1 = VO2

To calculate the Rotation between the frames

VC = C1 - C2 = (5,0)
VL = L1 - L2 = (5,0)
UnitVC = (1,0)
UnitVL = (1,0)
angle = UnitVC • UnitVl (dotProduct)
Rotation = cosine(angle)^(-1)
Rotation = cosine(1)^(-1) = 0

With the offset vector VO and the rotation between the planes, any coordinates the camera system outputs to the laser can be mapped

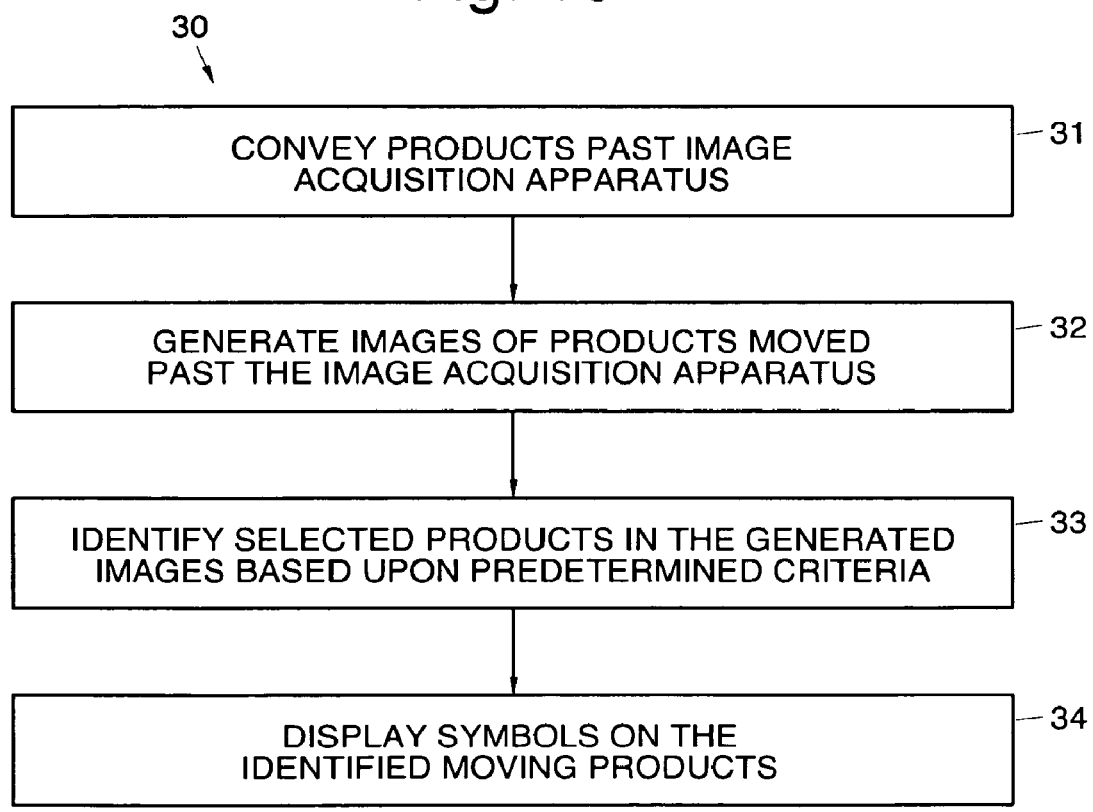

AUGMENTED REALITY INDUSTRIAL OVERLINE SYSTEMS AND METHODS

BACKGROUND

The present invention relates generally to industrial overline systems and methods, such as baking, cooking and routing systems, and more particularly, to augmented reality vision-based industrial overline systems and methods for monitoring and controlling baking, cooking and routing processes.

Conventional baking, cooking and routing processes, and the like, have the goal of providing efficient throughput of product conveyed along a conveyor belt. For example, buns produced for fast food providers have different specifications, and it is desirable to have automated high-volume baking systems that can detect out-of-spec product and remove defective buns from the conveyor belt. Similarly, cooked poultry transferred out of an oven is randomly located and oriented on the conveyor belt and it is desirable to detect product that is over-cooked or under-cooked. The defective buns or poultry is typically detected by an operator (inspector) and removed from the conveyor belt.

In the case of routing processes, labels may be used for routing within a distribution center. Such labels are applied to packages when they arrive at the distribution center, and are used to route the packages to appropriate delivery trucks. This process involves printing and applying thousands of labels, and a solution is desired to automate aspects of the internal routing process to reduce the number of labels that are necessary.

It would be desirable to have augmented reality vision-based systems and methods that monitor and control baking, cooking and routing processes, and the like. It would be desirable to have an augmented reality monitoring system that includes a projection display system or a laser projection system that is networked with an infrared or visible imaging system that improves the ability to monitor and control baking, cooking and routing processes, and the like. It would also be desirable to have an augmented reality monitoring system comprising a barcode reader, a projection display system or a laser projection system, and an infrared or visible imaging system that are networked together and which improves the ability to monitor and control baking, cooking and routing processes, and the like.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 5 illustrates a third exemplary embodiment of the augmented reality industrial overline system;

FIGS. 6a-6c illustrate exemplary tracking of product between fields of view of a camera system and a laser or LCD projection system;

FIG. 10 illustrates exemplary augmented reality product processing methods.

DETAILED DESCRIPTION

Described herein are augmented reality industrial overline systems and methods. The augmented reality systems and methods may be employed to monitor and control baking, cooking and routing processes, and the like. Exemplary reduced-to-practice embodiments of the augmented reality systems and methods may be used for overline monitoring, inspection and control of processes relating to raw and cooked meat, vegetables and baked items. Exemplary reduced-to-practice systems and methods may also be used to monitor, inspect and control package tracking and delivery processes.

Figure 1:
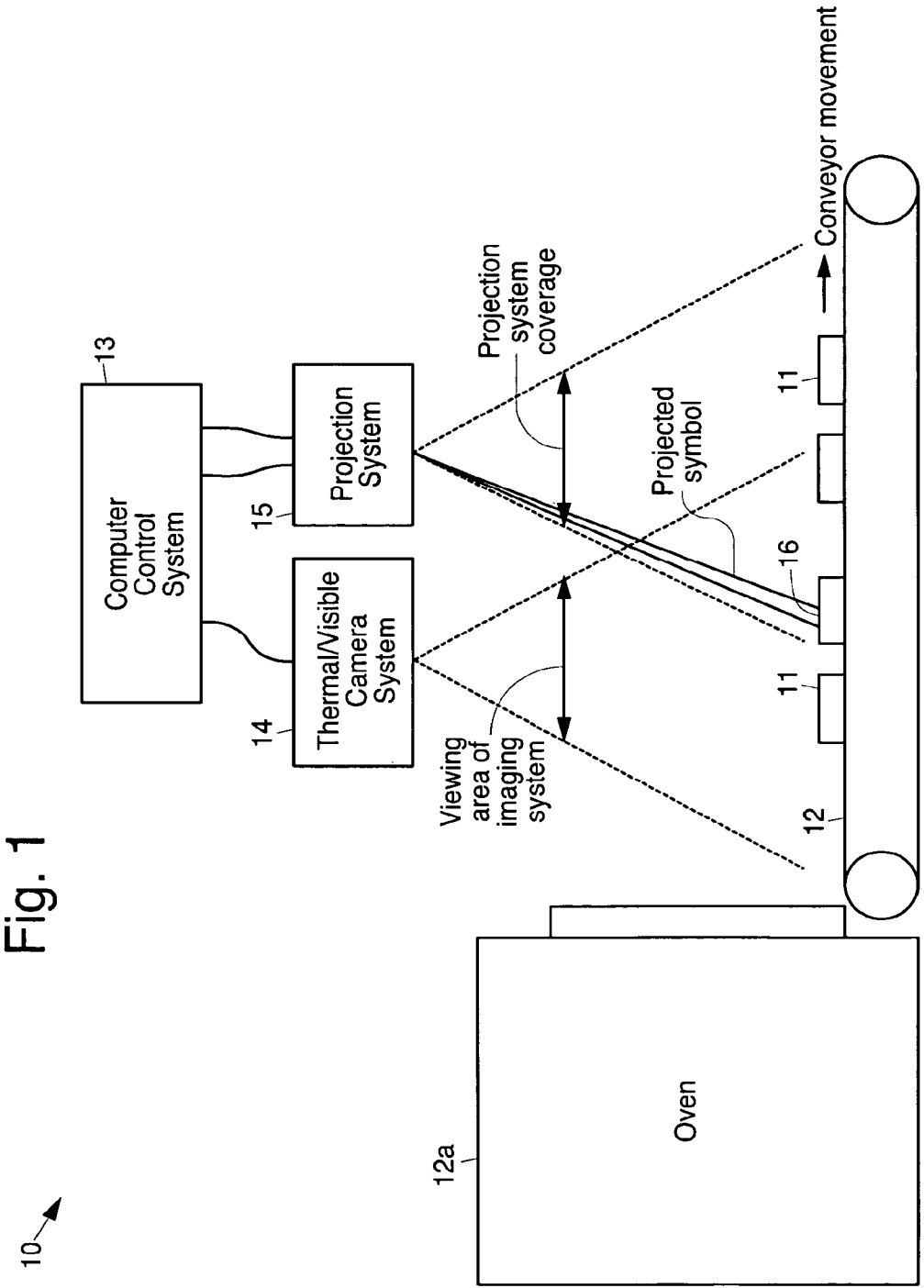
FIG. 1 illustrates a first exemplary embodiment of an augmented reality industrial overline system.

Referring to the drawing figures, FIG. 1 illustrates a first exemplary embodiment of an augmented reality industrial overline system 10. The first exemplary embodiment of the system 10 comprises an oven 12a that may be used to process product 11, such as to cook poultry or bake buns, for example. The exemplary system 10 displays identifying or instructional information directly on cooked or baked product 11 as it is moved by a conveyor 12 after exiting the oven 12a.

The identifying or instructional information is generated by networking an imaging system 14 (or image acquisition system 14) with a projection system 15 comprising a symbol generation system 15. The imaging system 14 may comprise an infrared (thermal) camera system 14 or a visible camera system 14, for example. The projection system 15 may comprise a laser projection system 15 or a liquid crystal display (LCD) projection system 15, for example. The imaging system 14 and the projection system 15 are coupled to and are controlled by a computer control system 13.

The imaging system 14 provides location information relating to product 11 transported by the conveyor 12. The use of an infrared camera system 14 provides location information and generates temperature information relating to the product 11 as it is transported by the conveyor 12. The temperature information is indicative of product temperature as the product moves out of the oven 12a.

The computer control system 13 comprises software 20 (FIGS. 6 and 7) that, when used with the thermal camera system 14, compares product temperature data with predetermined low and/or high temperature thresholds. When the temperature of a particular product 11 is lower than or exceeds one of the predetermined thresholds, the software 20 running on the computer control system 13 causes the projection system 15 to project information onto specific product 11 that is under or over the desired temperature, based on the monitored temperature data.

The projected information may be a symbol 16 or other indicator identifying the defective (over- or under-temperature) product 11. Suitable symbols 16 may be a cross, a plus sign, small or large dots, a star, or any other readily visible symbol 16 that is projected on and moves along with the defective product 11. The symbols 16 may be projected with any desired color that makes it visible to an operator. In exemplary reduced-to-practice embodiments of the system 10, red and green colored symbols were used in tests to determine their efficacy. The product 11 that is illuminated by the projected symbols 16 is removed from the conveyor 12 by the operator.

FIGS. 9a-9d show photographs illustrating various colored symbols 16 that may be used to identify defective product 11. The color of the symbol 16 is typically selected to maximize contrast with the color of the product 11. Prototype systems 11 have been developed and tested with a variety of projected shapes and colors to allow for the best possible transmission of instructions to operators monitoring the conveyor 12.

Figure 2:
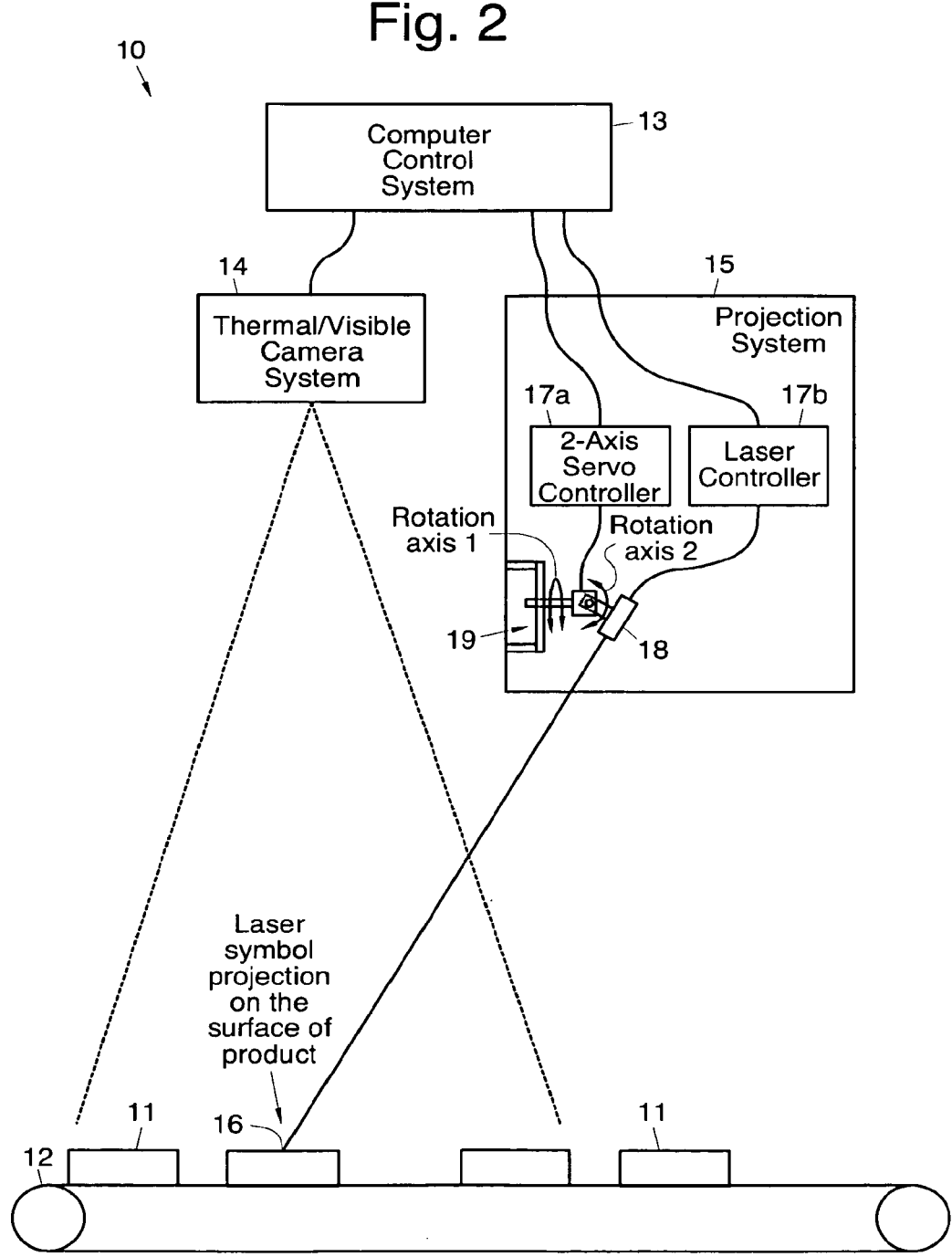
FIG. 2 illustrates details of one implementation of the exemplary augmented reality industrial overline system shown in FIG. 1.

A number of prototype systems 10 were developed to test capabilities of the various embodiments. As is illustrated in FIG. 2, one prototype system 10 comprises a visible/thermal camera system 14 and a laser projection system 15 employing a pan-and-tilt laser pointing system 19. The laser projection system 15 comprises a laser 18 that may be mounted on the pan-and-tilt laser pointing system 19. A two-axis servo beamsteering controller 17a is coupled to and controls the pan-and-tilt laser pointing system 19 to point the beam of the laser 18 onto the product 11. An exemplary two-axis servo beamsteering controller 17a may be a Mini-ITX central processing unit (CPU). The two-axis servo beamsteering controller 17a is controlled via the software 20 to move the laser 18, and thus its laser beam or spot 16, and move the laser spot 16 along with the moving product 11.

By sending control commands to the two-axis beamsteering controller 17a from the computer control system 13, the laser light is projected onto product 11 on the conveyor 12. The control software 20 is calibrated to synchronize laser beam locations on the conveyor 12 with corresponding locations generated by the camera system 14. A laser controller 17b turns the laser 18 on and off under control of software 20 running on the computer control system 13.

Figure 3:
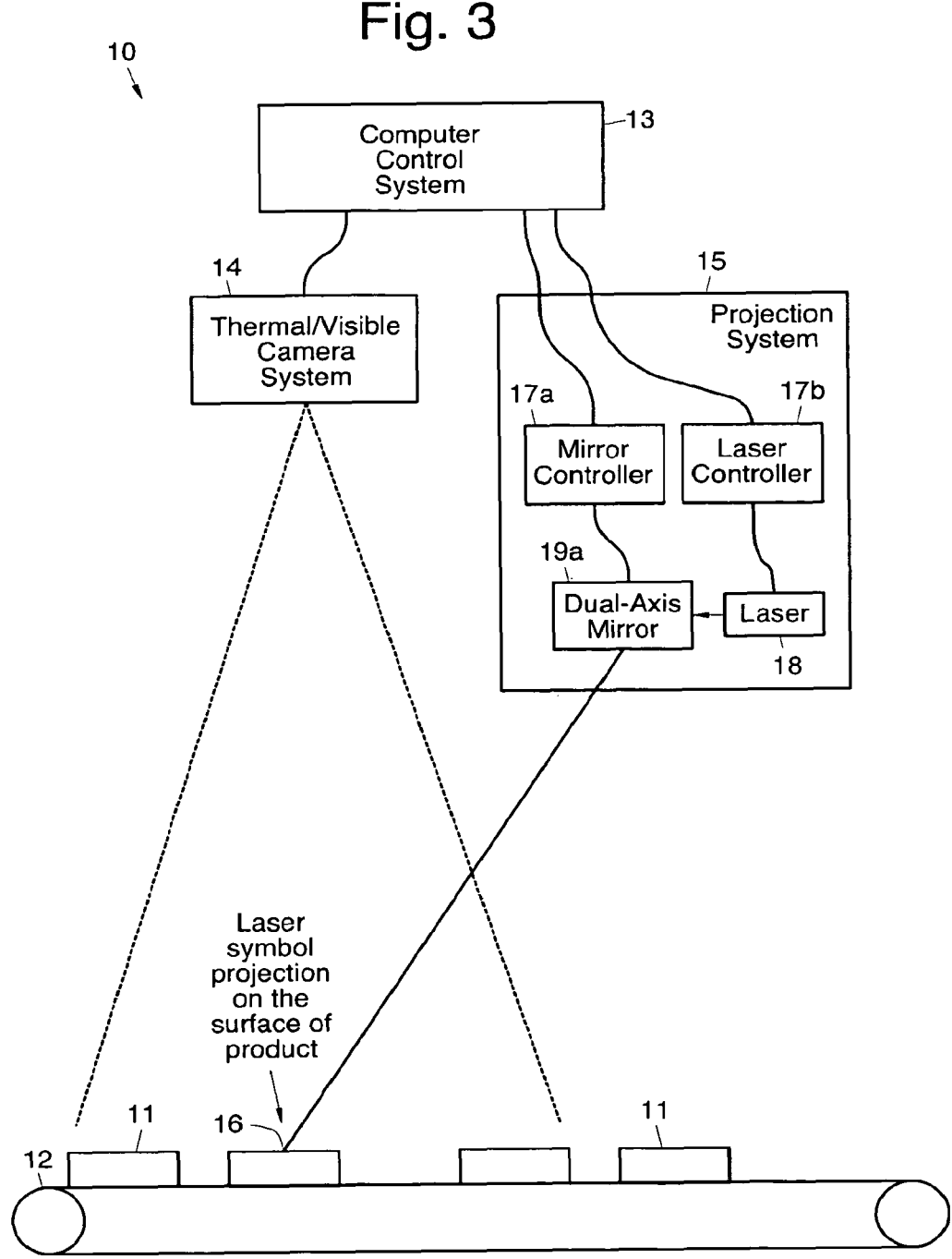
FIG. 3 illustrates details of another implementation of the exemplary augmented reality industrial overline system shown in FIG. 1.

As is illustrated in FIG. 3, another prototype system 10 comprises a visible/thermal camera system 14 and a laser projection system 15 employing a dual axis mirror 19a and mirror beamsteering controller 17a. The dual axis mirror 19a is controlled by galvanometer circuitry that allows rapid movement of the mirror to point the beam of the laser 18 onto the product 11 and create the symbol pattern.

Figure 4:
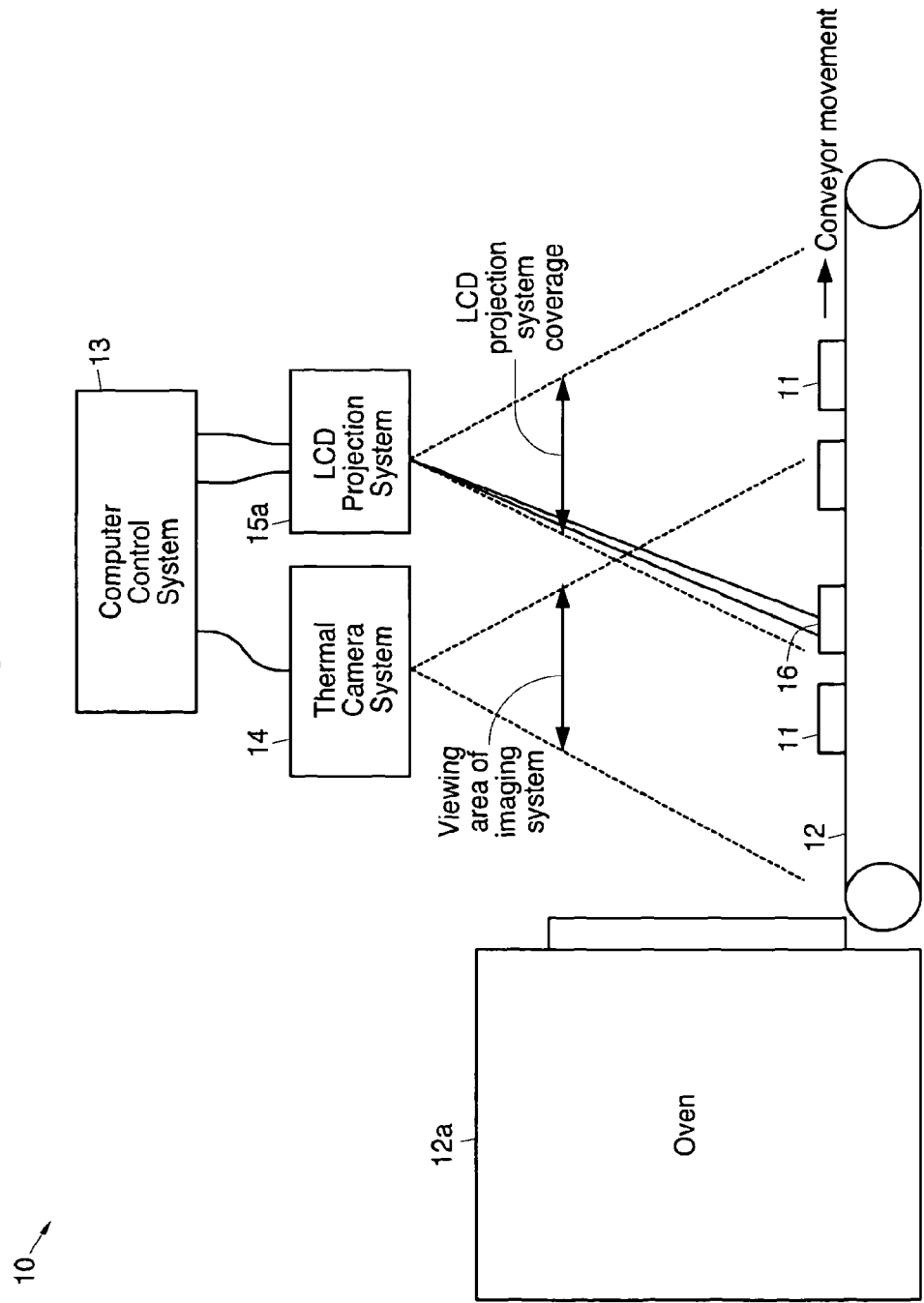
FIG. 4 illustrates a second exemplary embodiment of the augmented reality industrial overline system.

As is illustrated in FIG. 4, another prototype system 10 comprises a thermal camera system 14 and a liquid crystal display (LCD) projector 13 mounted above the conveyor 12. The thermal camera system 14 and LCD projector 13 are coupled to and are controlled by the computer control system 13. This embodiment of the system 10 may be used in conjunction with baking or cooking processes employing the oven 12a. Cooked or baked product 11 exiting the oven 12a is transported by the conveyor 12 under the thermal camera system 14 and projector 13. The thermal camera system 14 is used to detect the temperature of the product 11. The temperature data is passed to the computer control system 13, and the software 20 running thereon compares the product temperature data with low and/or high temperature thresholds and identifies defective (uncooked or overcooked) product 11, for example. The thermal camera system 14 also provides location data to the software 20. The software 20 controls the LCD projection system 15a and causes it to project a symbol 16 onto the defective product 11 as it is moved by the conveyor 12. An operator can then remove the defective product 11 from the conveyor 12 that is identified by the symbol 16.

More particularly, laser control algorithms of the software 20 process the location information found through analysis of the digital images derived from the camera system 14 to update the location of a currently tracked product 11. When a new product 11 is tracked, the servo system 17a moves the laser beam to point at the correct location on the conveyor 12 and then turns on the laser 16 to controllably draw or project the desired symbol 16 or spot 16. The laser beam location is changed as information about the product location is updated. When the tracked product 11 moves out of range of the laser projection system 15, the laser 18 is turned off and the laser control system 15 waits for further product location information.

FIG. 5 illustrates yet another prototype system 10 comprising a visible/thermal camera system 14 and a laser/LCD projection system 15, 15a. This embodiment of the system 10 preferably used a visible camera system 14 and a laser projection system 15 employing a dual axis mirror 19a and a mirror beamsteering controller 17a. In addition, the system 10 further comprises a barcode scanner 12b that is used to identify product 11 (packages 11 or items 11) having barcode labels 12c disposed thereon. By way of example, the barcode label 12c may contain tracking information relating to the product 11 or package 11. The computer control system 13, camera system 14 and projection system 15, under control of the software 20, are used to track the packages 11 as they move along the conveyor 12 and display a delivery truck identifier, for example, such as a truck number, for example, on each package 11 so that it can be taken off of the conveyor 12 by a driver or operator and loaded onto an appropriate delivery truck.

In order to properly track product 11 as it moves from the field of view of the visible/thermal camera system 14 to the field of view of the laser 18 or LCD projection system 15a, locations viewed by the visible/thermal camera system 14 are mapped to coordinates within the field of view of the laser 18 or LCD projection system 15a.

Figure 6A:
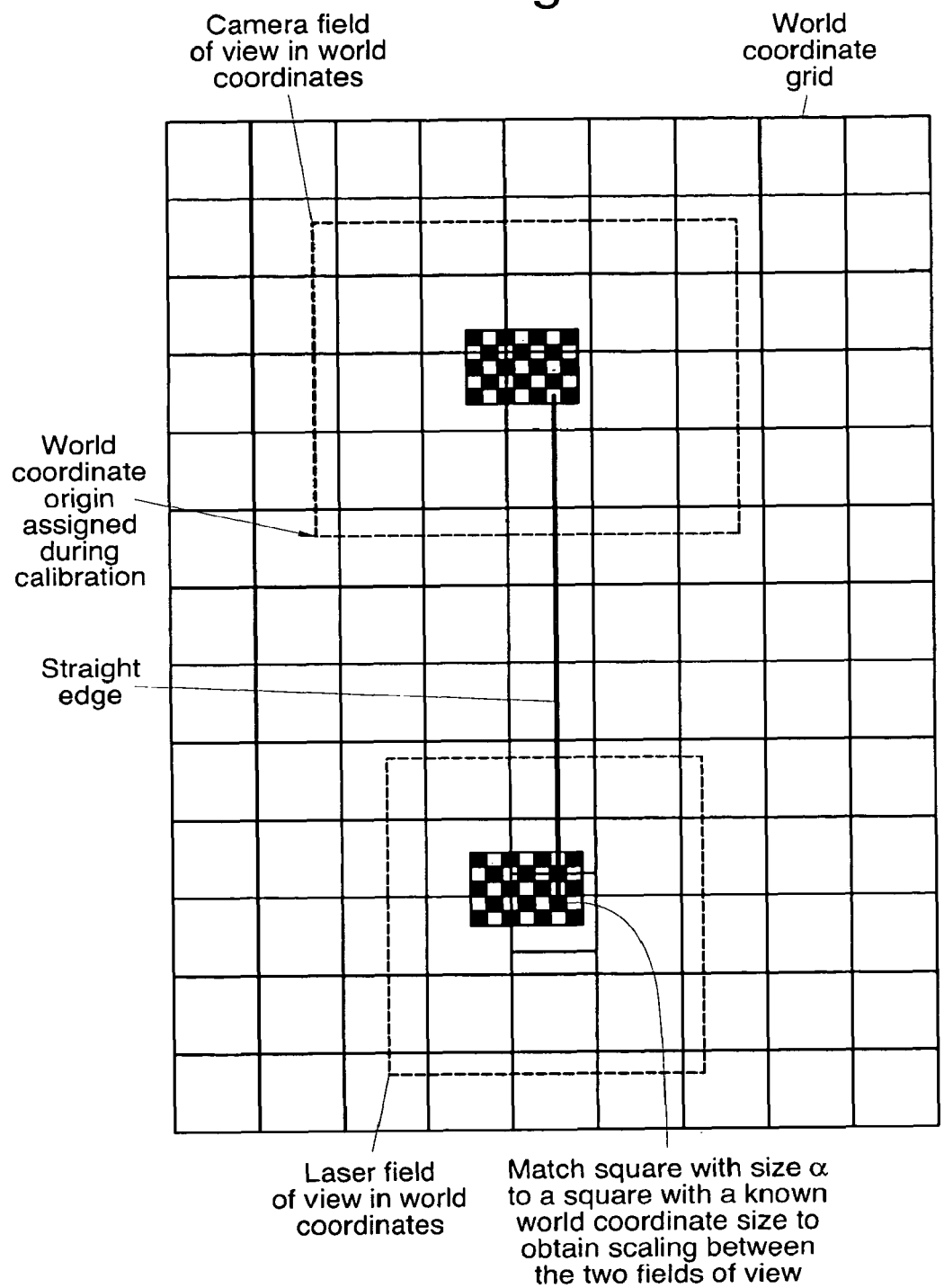
Figure 6B:
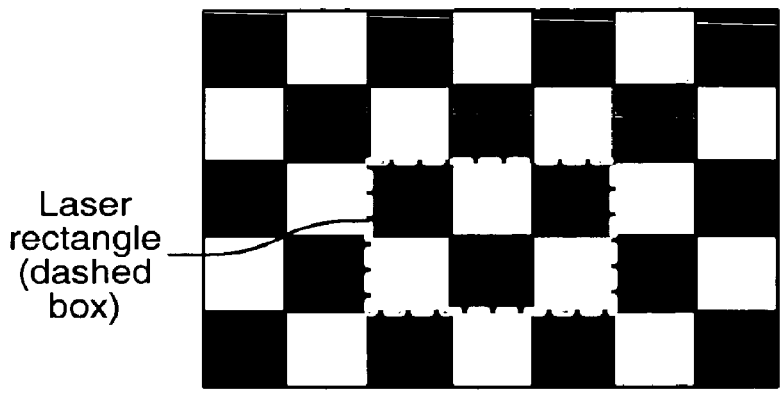

FIGS. 6a-6c illustrate exemplary tracking of product between fields of view of the camera system 14 and laser 18 or LCD projection system 15a. FIG. 6a shows an exemplary world coordinate system encompassing the fields of view of the camera system 14 and laser 18 or LCD projection system 15a. A world coordinate system (large grid) is defined. A world coordinate origin for a camera image frame is assigned during calibration of the camera system 14. A straight edge may be used to define two points in laser world coordinates and two points in camera world coordinates. Two points in each frame with the known vector between them the gives us translation and rotation. A square with size a may be matched to a square with a known world coordinate size to obtain scaling between the two fields of view.

FIG. 6b shows an exemplary checkerboard grid with a representative laser grid (the six squares surrounded by a dashed box). A representative example of how to determine the relationship between world units and laser units is shown. In the example, the checkerboard square corresponds to 3×3 world units (cm, in, etc.), the laser rectangle is 3×2 CS (data transferred to the software 20), and the laser rectangle is 30×20 laser units (known by the software 20). Thus, 3×2 checkerboard squares=30×20 laser units, 1 checkerboard square=10×10 laser units, 3×3 world units=10×10 laser units, 1 laser unit=0.3 world units or 1 world unit=3.33 laser units.

FIG. 6c shows an example of a translation of locations in the camera field of view to locations in the laser field of view. By way of example, frame respective units may be defined as:

C1=(100, 100) in the camera,

C2=(105, 100) in the camera,

L1=(10, 20) in the laser,

L2=(20, 20) in the laser.

Camera software picks origin of world units and assigns C1 to WC1 and C2 to WC2:
    WC1=(30, 10),
    WC2=(35, 10).
The length of the yardstick is known and is:
    V=(0, 300).
Where WL1 and WL2 are can be calculated using a vector V:
    WL1=C2−V,
    WL2=C2−V,
    WL1=(30, 10)−(0,300)=(30, −290),
    WL2=(35, 10)−(0,300)=(35, −290).
Since we know the scaling we can find where the laser origin is in world units, and the vector VO which defines the offset
    VO1=WL1−(L1*scaling),
    VO2=WL2−(L2*scaling),
    VO1=VO2.
To calculate the amount of rotation between the frames:
    VC=C1−C2=(5,0),
    VL=L1−L2=(5,0),
    UnitVC=(1,0),
    UnitVL=(1,0),
    angle=UnitVC·UnitVl (dotProduct),
    Rotation=cosine(angle)^(−1), and
    Rotation=cosine(1)^(−1)=0.
With the offset vector VO and the rotation between the planes any coordinates the camera system outputs to the laser can be mapped.

Figure 7:
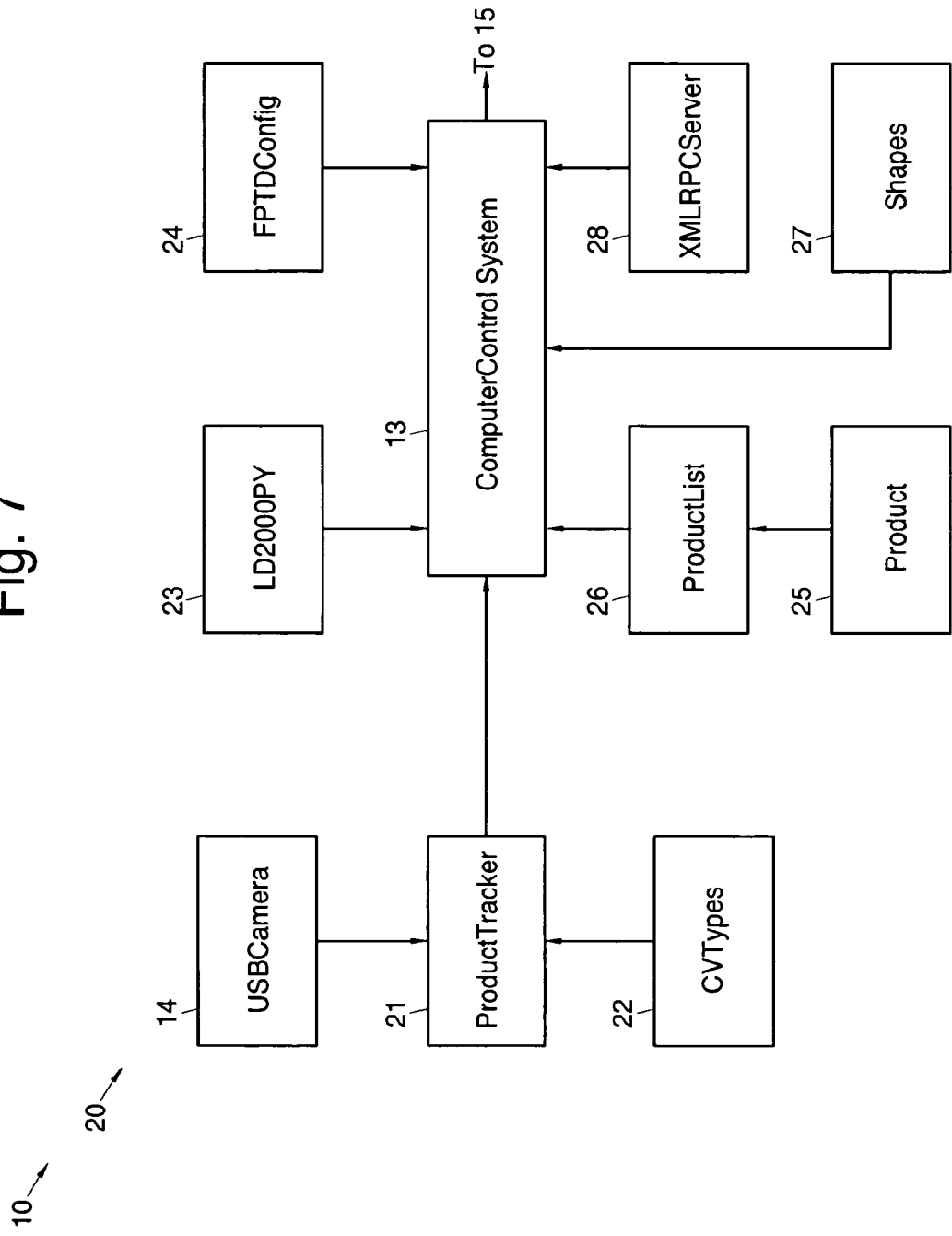
FIG. 7 illustrates software that may be employed in the augmented reality systems shown in FIGS. 1-3.
Figure 8:
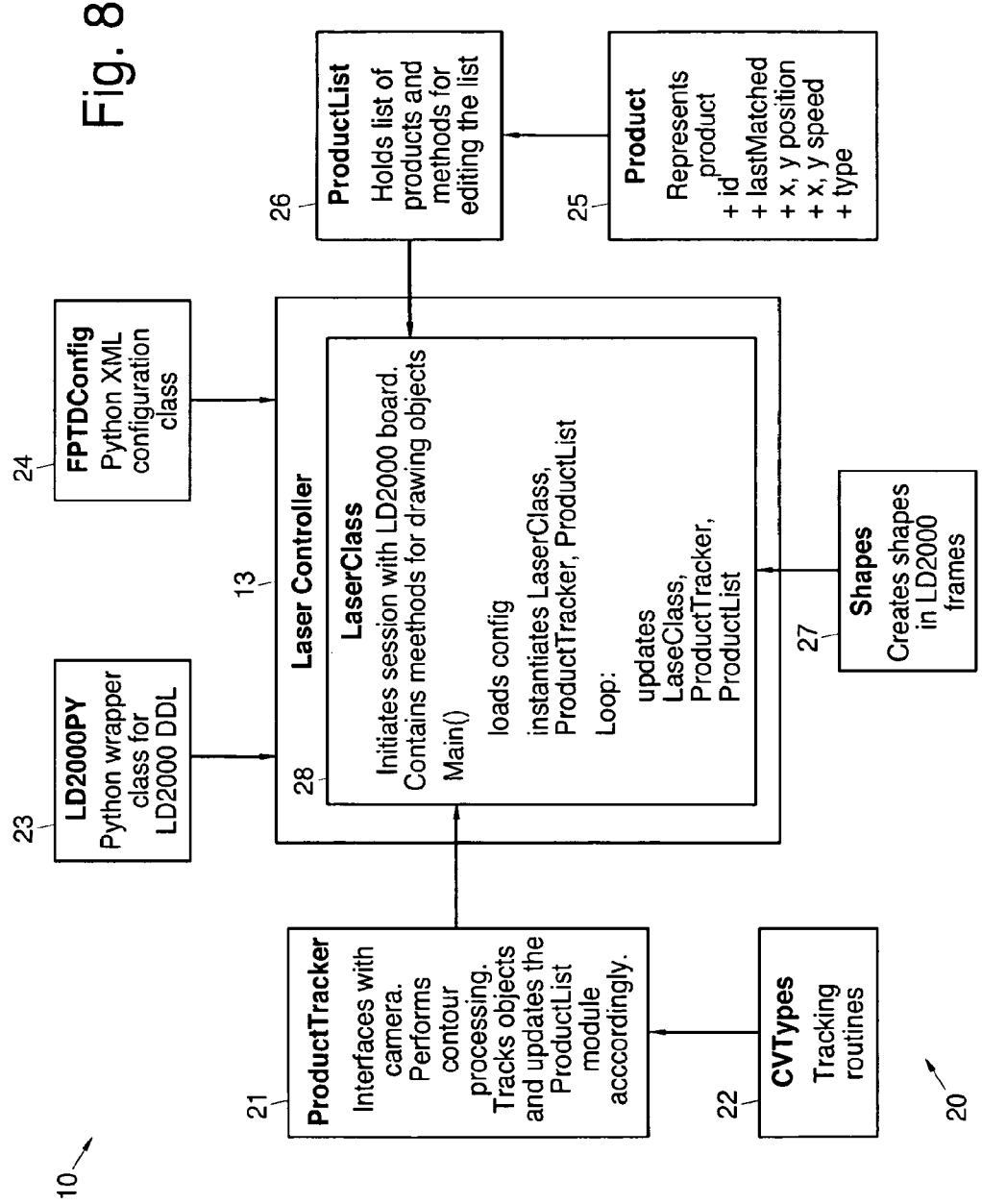
FIG. 8 illustrates details of the software shown in FIG. 6.
Figure 9A:
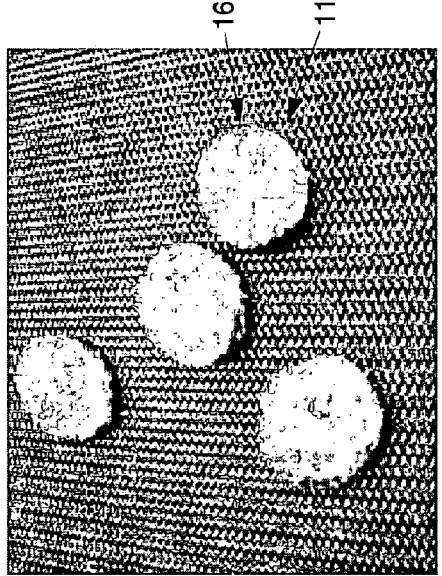
FIGS. 9a-9d show photographs illustrating various colored symbols used to identify defective product.
Figure 9B:
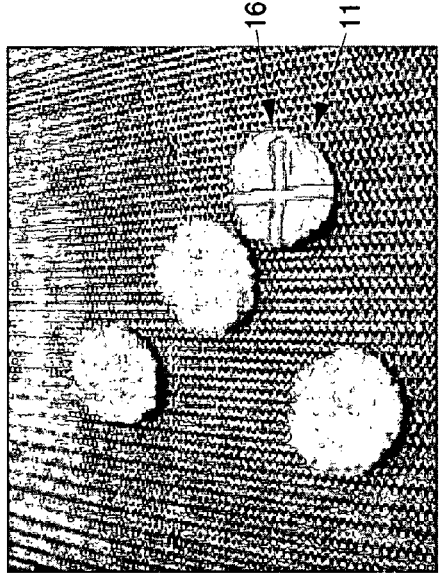
Figure 9C:
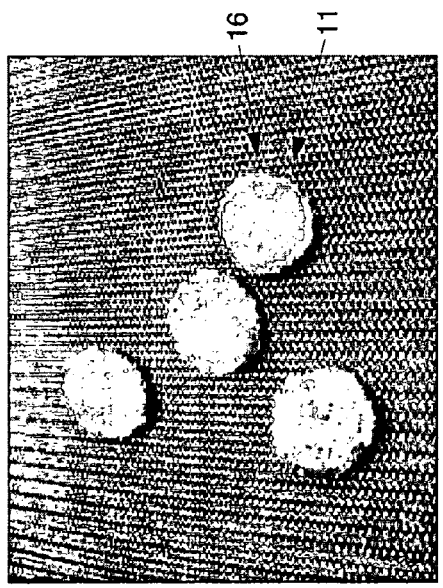
Figure 9D:
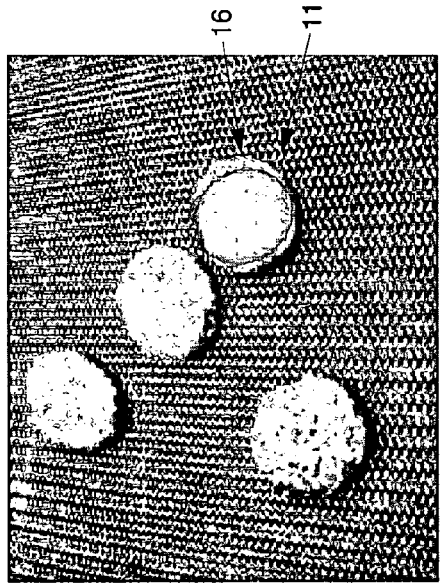

FIG. 7 illustrates exemplary software 20 that may be employed in the augmented reality systems 10 shown in FIGS. 1-5. FIG. 8 illustrates details of the exemplary software 20 shown in FIG. 7. The exemplary software 20 is implemented in the computer control system 13. The exemplary software 20 provides for product tracking using the visible/thermal camera system 14 and control of the beamsteering controller 17a and laser 18 or LCD projection system 15a.

The tracking camera system 14 outputs digital image frames to a ProductTracker module 21. A CVTypes module 22 is a Python programming language wrapper interface to a well-known OpenCV computer vision software library that contains routines that allow the ProductTracker module 21 to perform image processing necessary to track objects based on the camera images. The OpenCV software library is a computer vision library of open-source software routines originally developed by Intel. The OpenCV software library is a cross-platform library is designed for real-time image processing applications. Routines have been developed that are embedded in the ProductTracker module 21 and provide for product motion tracking.

The ProductTracker module 21 performs image thresholding and contour processing to track objects (product 11) in the digital image frames, and updates a ProductList module 26 accordingly. A Product module 25 stores data that corresponds to or represents the product 11. The data stored in the Product module 25 may include a product identifier (id), a lastMatched time-stamp identifier, an x, y position of the product 11 in the digital image frame, an x, y speed of the product 11, and product type, for example. The data stored in the Product module 25 is input to the ProductList module 26.

An LD2000PY module 23 is a Python high-level object-oriented programming language wrapper class for a Laser-show Designer LD2000 DLL (dynamically linked library) provided with the LD2000 laser controller hardware by Pangolin Systems. The Python programming language wrapper is used to interface to other application programming interfaces. An application programming interface (API) is well-known to software programmers, and is a set of routines, data structures, object classes and/or protocols provided by libraries and/or operating system services in order to support the building of applications.

The LD2000PY module 23 comprises a laser controller application programming interface that outputs control signals to an LD2000 controller 17a that is coupled to the dual-axis mirror 19a, for example. An FPTDConfig module 24 is a well-known Python XML (extensible markup language) configuration class that implements XML parsing. The FPTD-Config module 24 stores configuration settings for the various software modules. The configuration settings stored in the configuration file include calibration values for translating between tracking camera, inspection system camera and laser coordinate systems, the direction of the conveyor belt, and other settings for the specifying how the tracking algorithms should function. A Shapes module 27 creates symbol shapes in LD2000 frames and outputs a selected shape that is generated by the projection system 15. The Shapes module generates a series of LD2000PY commands specifying a sequence of relative x, y coordinate locations to point the laser that comprises a frame for the LD2000 laser projection module. The LD2000 laser projection module then moves the laser repeatedly to draw the corresponding shape on the product. An XMLRPCServer module 28 provides an interface between the inspection system 14 and the projection system 15. The XMLRPCServer is an network server uses the well known XMLRPC protocol for relaying information. A LaserClass module 28 is coupled to the ProductTracker module 21, the LD2000PY module 23, the FPTDConfig module 24, the ProductList module 26, and the Shapes module 27. The LaserClass module 28 interfaces with the laser controller 13 to control drawing of symbols 16 by the laser 18.

More particularly, the software 20 running on the laser controller 13 initiates a session with the LD2000 controller 17a. The software 20 loads configuration files from the FPTDConfig module 24, and then instantiates the LaserClass, ProductTracker and ProductList modules 28, 21, 25. The ProductTracker module 21 interfaces with and processes digital image frames output by the camera system 14 using OpenCV software routines in the CVTypes module 22. The ProductTracker module 21 performs image thresholding and contour processing to identify individual products 11 in the image frame and tracks the products 11 from frame to frame. The ProductTracker module 21 updates a list of products 11 contained in the ProductList module 26. The Product module 25 contains data representative of products 11 that are stored in the ProductList module 26. The LaserClass module 28 processes iteratively obtains product location data derived from the ProductTracker module 21 that is stored in the ProductList module 26 and uses routines in the LD2000PY module 23 and a selected symbol shape from the Shapes module 27 to generate an appropriate symbol 16 on the product 11 as is conveyed by the conveyor 12. The LaserClass module 28 updates the LaserClass ProductTracker, and ProductList modules 28, 21, 26 as the product 11 moves with the conveyor 12. The software 20 thus generates one or more symbols 16 that illuminate and move along with the product 11 as it is conveyed by the conveyor 12.

After initialization of components as discussed above, the overall software system implements a loop that runs methods in the modules in sequence:

(1) The ProductTracker modules 21 is run to find moving product in the view of the tracking camera 14 and update the ProductList module 25;

(2) The XMLRPCServer module 28 receives inspection system locations about out-of-spec product and updates the ProductList module 25;

(3) A ProductList method is called to clear out old Product items and update current locations of Product items; and (4) The LaserClass module 28 updates the locations of projected symbols 16 based on the ProductList by estimating the current locations using the x, y locations and timestamp in each of the Product items.

FIGS. 9a-9d show photographs illustrating tests involving the use of different colored symbols to identify defective product 11. In particular, FIGS. 9a-9d show photographs of frozen breaded chicken product 11 moved by the conveyor 12. In the tests, an LCD projection system 15a, for example, was coupled to the computer control system 13 which includes a display that overlays the product 11 on the conveyor 12 with various symbols 16. In these tests, green symbols 16 showed up much better than red symbols 16 on breaded chicken product. However, both colors were visible even though there were bright florescent lights in the test area.

for the purposes of completeness, FIG. 10 illustrates an exemplary augmented reality product processing method 30. The Exemplary method 30 comprises conveying 31 products 11 past image acquisition apparatus 14. Images of products 11 are generated 32 as the products 11 move past the image acquisition apparatus 14. Selected products in the generated images are identified 33 based upon predetermined criteria. Symbols are displayed 34 on the identified products as they are conveyed.

Thus, exemplary product processing systems 10 and methods 30 have been disclosed that comprise a conveyor 12 for moving products 11, an image acquisition system 14 for generating images of products 11 moved by the conveyor 12 and a symbol generation system for processing the generated images and for displaying symbols 16 on selected products 11 moved by the conveyor 12 based upon predetermined criteria. The product processing systems 10 may be used to process oven-cooked or oven-baked products 11 to identify (using projected symbols 16) products 11 that are defective or otherwise unacceptable. The product processing systems 10 may be used to process packages 11 or items 11 having barcodes or other identifying labels thereon to display routing or other identifying information on the products 11 move by the conveyor 12. Exemplary product processing methods 30 have also been disclosed that are used to monitor and display processing related information on products 11 moved by the conveyor 12.

Thus, augmented reality vision-based industrial overline systems and methods for monitoring, inspecting and controlling baking, cooking and routing processes, and the like, have been disclosed. It is to be understood that the above-described embodiments are merely illustrative of some of the many specific embodiments that represent applications of the principles discussed above. Clearly, numerous and other arrangements can be readily devised by those skilled in the art without departing from the scope of the invention.

What is claimed is:

1. Apparatus, comprising:
    a conveyor for moving products;
    an image acquisition system for generating images of products moved by the conveyor; and
    a symbol generation system coupled to the image acquisition system for processing the generated images and for displaying symbols on selected products moved by the conveyor based upon predetermined criteria, the symbol generation system comprising a laser projection system.

2. The apparatus recited in claim 1 further comprising a product processor for processing product that is transferred onto the conveyor.

3. The apparatus recited in claim 2 wherein the product processor comprises an oven and wherein the conveyor is operative to move products cooked or baked in the oven.

4. The apparatus recited in claim 1 which comprises software algorithms that:
    generates images of products moved past the image acquisition apparatus;
    identifies selected products in the generated images based upon predetermined criteria; and
    displays symbols on the identified products moved by the conveyor.

5. The apparatus recited in claim 1 wherein the image acquisition system comprises a visible imaging system.

6. The apparatus recited in claim 1 wherein the image acquisition system comprises a thermal imaging system.

7. Apparatus, comprising:
    a conveyor for moving products;
    an image acquisition system for generating images of products moved by the conveyor; and
    a symbol generation system coupled to the image acquisition system for processing the generated images and for displaying symbols on selected products moved by the conveyor based upon predetermined criteria, the symbol generation system comprising a liquid crystal display (LCD) projection system.

8. Apparatus, comprising:
    a conveyor for moving products;
    an image acquisition system for generating images of products moved by the conveyor; and
    a symbol generation system coupled to the image acquisition system for processing the generated images and for displaying symbols on selected products moved by the conveyor based upon predetermined criteria, the symbol generation system comprising a pan-and-tilt laser pointing system.

9. Apparatus, comprising:
    a conveyor for moving products;
    an image acquisition system for generating images of products moved by the conveyor; and
    a symbol generation system coupled to the image acquisition system for processing the generated images and for displaying symbols on selected products moved by the conveyor based upon predetermined criteria, the symbol generation system comprising a dual axis mirror beam-steering system.

10. The apparatus recited in claim 1 further comprising a bar code reader for identifying product on the conveyor.

11. Apparatus, comprising:
    an oven;
    a conveyor for moving products cooked or baked in the oven;
    an image acquisition system for generating images of products moved by the conveyor;
    a symbol generation system coupled to the image acquisition system for processing the generated images and for displaying symbols on selected products moved by the conveyor based upon predetermined criteria related to temperatures of the products; and
    software algorithms that:
        generate images of products moved past the image acquisition apparatus;
        identify selected products in the generated images based upon temperatures of the products; and display symbols on the identified products moved by the conveyor.

12. Apparatus, comprising:

a conveyor for moving products having identifiers thereon;

an image acquisition system for generating images of products moved by the conveyor; and a symbol generation system coupled to the image acquisition system for processing the generated images and information corresponding to the identifiers, and for projecting symbols on selected products moved by the conveyor based upon the information contained in the identifiers.

13. The apparatus recited in claim 12 further comprising a bar code reader for reading the identifiers to identify the products on the conveyor to generate the information corresponding to the identifiers.

14. A method comprising:

conveying products past image acquisition apparatus;

generating images of products moved past the image acquisition apparatus; identifying selected products in the generated images based upon predetermined criteria; and projecting symbols on the identified products as they are conveyed.

15. The method recited in claim 14 further comprising, determining locations of conveyed products in the images;

tracking the locations of the conveyed products as they are conveyed;

projecting symbols on the identified products as they are conveyed.

16. The method recited in claim 14 further comprising removing the identified products from products that are conveyed past the inspection apparatus.

17. The method recited in claim 14 wherein the predetermined manner of processing the products is selected from a group including cooking, baking, and routing.

18. The method recited in claim 14 further comprising: tracking the conveyed products using barcodes.

* * * * *